United States Patent
Lee et al.

(10) Patent No.: US 9,882,147 B2
(45) Date of Patent: Jan. 30, 2018

(54) DELAYED FLUORESCENCE MATERIAL AND ORGANIC LIGHT EMITTING DEVICE HAVING THE DELAYED FLUORESCENCE MATERIAL

(71) Applicant: RESEARCH & BUSINESS FOUNDATION SUNGKYUNKWAN UNIVERSITY, Suwon-si (KR)

(72) Inventors: Jun Yeob Lee, Seoul (KR); Yu Jin Kang, Incheon (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/281,431

(22) Filed: Sep. 30, 2016

(65) Prior Publication Data

US 2017/0098779 A1    Apr. 6, 2017

(30) Foreign Application Priority Data

Oct. 2, 2015    (KR) .................. 10-2015-0139332

(51) Int. Cl.
| | | |
|---|---|---|
| *H01L 51/00* | (2006.01) | |
| *C09K 11/06* | (2006.01) | |
| *C07D 491/048* | (2006.01) | |
| *H01L 51/50* | (2006.01) | |

(52) U.S. Cl.
CPC ...... *H01L 51/0071* (2013.01); *C07D 491/048* (2013.01); *C09K 11/06* (2013.01); *H01L 51/0067* (2013.01); *C09K 2211/1007* (2013.01); *C09K 2211/1029* (2013.01); *C09K 2211/1033* (2013.01); *C09K 2211/1059* (2013.01); *H01L 51/5016* (2013.01); *H01L 2251/5376* (2013.01)

(58) Field of Classification Search
CPC .......... C07D 491/048; C09K 11/06; C09K 2211/1007; C09K 2211/1029; C09K 2211/1033; C09K 2211/1059; H01L 2251/5376; H01L 51/0067; H01L 51/0071; H01L 51/5016
See application file for complete search history.

(56) References Cited

FOREIGN PATENT DOCUMENTS

| CN | 106279203 | * | 4/2016 | ........... C07D 221/18 |
| JP | 20100267575 | * | 6/2012 | ........... C07D 471/04 |

* cited by examiner

*Primary Examiner* — Erich A Leeser
(74) *Attorney, Agent, or Firm* — NSIP Law

(57) ABSTRACT

A delayed fluorescence material in accordance with the present disclosure may comprise a compound having a molecular structure including an electron donor unit and an electron acceptor unit coupled to the electron donor unit, wherein the electron donor unit includes an acridine furan derivative formed by acridine being bonded to dibenzofuran. The delayed fluorescence material may allow high structural and thermal stabilities and improved quantum efficiency.

14 Claims, 1 Drawing Sheet

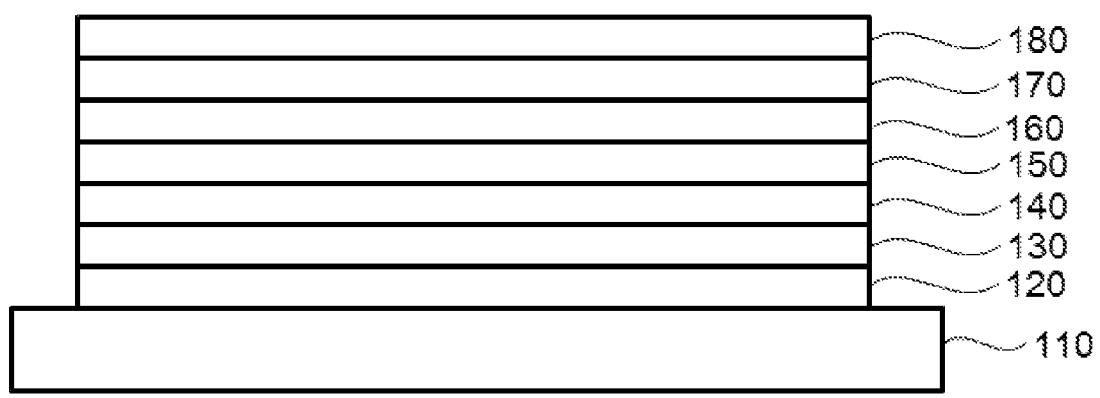

DELAYED FLUORESCENCE MATERIAL AND ORGANIC LIGHT EMITTING DEVICE HAVING THE DELAYED FLUORESCENCE MATERIAL

CROSS-REFERENCE TO RELATED APPLICATION

This application claims the benefit of Korea patent application No. 10-2015-0139332 filed on Oct. 2, 2015, the entire content of which is incorporated herein by reference for all purposes as if fully set forth herein.

BACKGROUND

Field of the Present Disclosure

The present disclosure relates to a delayed fluorescence material with long-time emission, and an organic light emitting device having the delayed fluorescence material.

Discussion of Related Art

To commercialize an organic light emitting device, a light emitting material should have an improved emission efficiency. For this, phosphorescence and delayed fluorescence materials have been studied actively. However, although the phosphorescence material achieves a high emission efficiency, the phosphorescence should employ a metal complex which is expensive and has a shot life-span.

As for the delayed fluorescence material, articles published in 『Nature』 (2012, 492, 234) and 『JACS』 (2012, 134, 14706) discloses TADF (Thermally Activated Delayed Fluorescence) to achieve high efficient green fluorescence materials with high external quantum efficiency. The TADF material is a substance that can up-convert a triplet excited state into a singlet excited state using a little thermal energy and efficiently exhibits light emission (fluorescence) from the singlet excited state. The fluorescence in this case is light emission from the excited singlet and hence is light emission at the same wavelength as fluorescence. However, the fluorescence has a longer lifetime of light to be emitted, i.e., a longer emission lifetime than those of normal fluorescence and phosphorescence by virtue of reverse intersystem crossing from an excited triplet state to an excited singlet state, and hence is observed as fluorescence delayed as compared to the normal fluorescence and phosphorescence. This can be defined as delayed fluorescence. In this connection, using a molecular structure including a combination of a donor unit to donate an electron and an acceptor unit to accept an electron, a small difference between the singlet and triplet excited energy states may be achieved to reach the efficient delayed fluorescence material. Since the delayed fluorescence material employs both the fluorescence light emitting and phosphorescence light emitting mechanisms, the delayed fluorescence material may remove the shortcoming of the existing fluorescence material; that is, the shortcoming in terms of the external quantum efficiency is eliminated and, further, it dispenses with the metal complex which is expensive and has a shot life-span.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The present disclosure is to provide a delayed fluorescence material having a molecular structure including an acridine furan derivative as an electron donor unit, thereby to achieve high structural and thermal stabilities and high triplet excited energy thereof.

The present disclosure is further to provide an organic light emitting device including the delayed fluorescence material.

In one aspect of the present disclosure, there is provided a delayed fluorescence material comprising a first compound having a molecular structure including an electron donor unit and an electron acceptor unit coupled to the electron donor unit, wherein the electron donor unit includes an acridine furan derivative formed by acridine being bonded to dibenzofuran.

In one embodiment, the first compound has a molecular structure expressed as a following chemical formula 1:

[chemical formula 1]

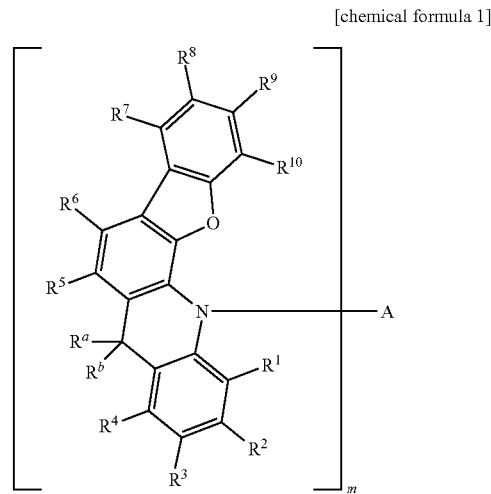

where, A indicates the electron acceptor unit; each of $R^1$ to $R^{10}$ and $R^a$ and $R^b$ individually indicates one selected from a group consisting of hydrogen, deuterium, an alkyl group with 1 to 60 carbon atoms, an alkenyl group with 2 to 60 carbon atoms, an alkynyl group with 2 to 60 carbon atoms, an aryl group with 6 to 60 carbon atoms, a heteroaryl group with 3 to 60 carbon atoms, an alkoxy group with 1 to 60 carbon atoms, an aryloxy group with 6 to 60 carbon atoms, an arylalkyl group with 7 to 60 carbon atoms, a heteroarylalkyl group with 3 to 60 carbon atoms, a cycloalkyl group with 3 to 60 carbon atoms, a heterocycloalkyl group with 1 to 60 carbon atoms, an alkylsilyl group with 3 to 60 carbon atoms, an arylsilyl group with 3 to 60 carbon atoms, and a heteroarylsilyl group with 1 to 60 carbon atoms; and m indicates 1 or 2.

In one embodiment, all of $R^1$ to $R^{10}$ indicate hydrogen or deuterium, wherein both of $R^a$ and $R^b$ indicate methyl groups respectively.

In one embodiment, the electron acceptor unit includes one functional group selected from a group consisting of functional groups expressed as following chemical formulas 2 to 6 respectively:

[chemical formula 2]

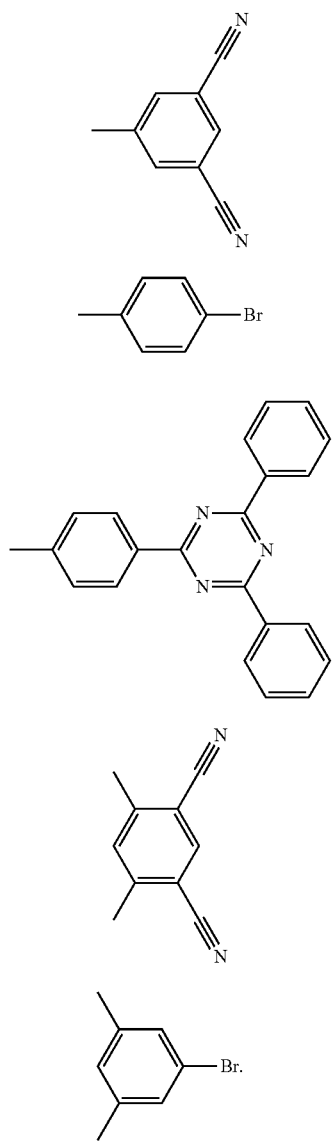

[chemical formula 3]

[chemical formula 4]

[chemical formula 5]

[chemical formula 6]

In one embodiment, the first compound has one molecular structure selected from a group of consisting of molecular structures expressed as following chemical formulas 7 to 10 respectively:

[chemical formula 7]

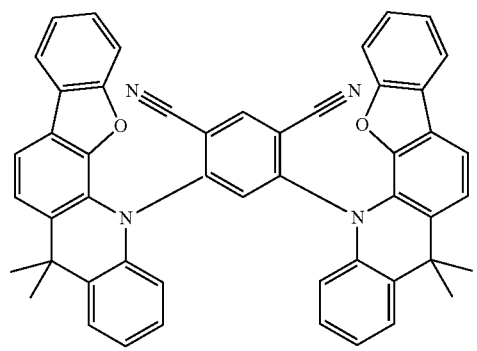

[chemical formula 8]

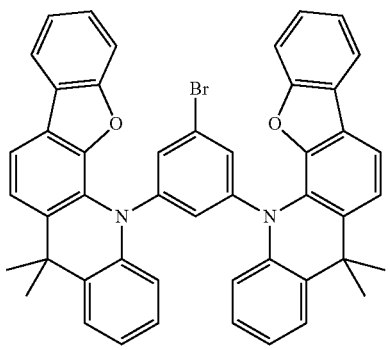

[chemical formula 9]

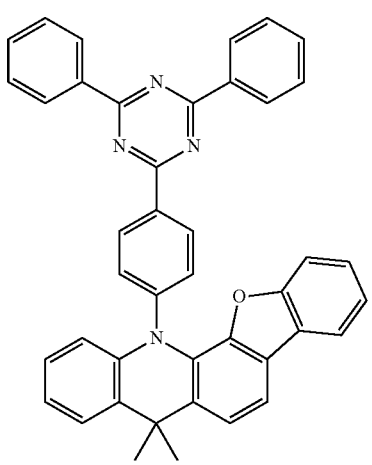

[chemical formula 10]

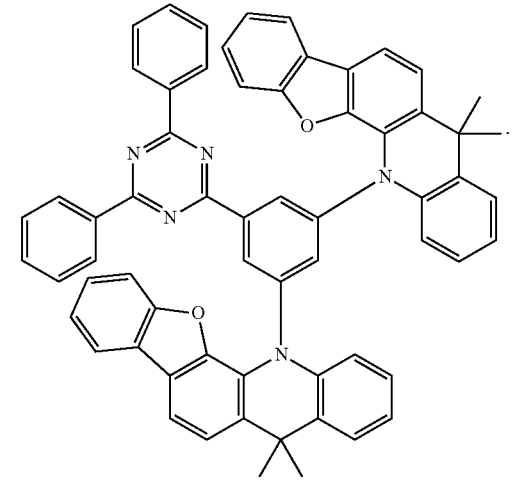

In another aspect of the present disclosure, there is provided an organic light emitting device including a light emitting layer containing the above-defined delayed fluorescence material.

In accordance with the present disclosure, the delayed fluorescence material includes, as the electron donor unit, the acridine furan derivative formed by the acridine being bonded to a meta location of the dibenzofuran. Thus, the acridine furan derivative as the electron donor unit may have not a planar or two-dimensional structure but a three-dimensional structure, to achieve higher structural and thermal stabilities and higher triplet excited energy thereof.

BRIEF DESCRIPTION OF THE DRAWINGS

FIG. 1 shows an organic light emitting device in accordance with the present disclosure.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, s, operations, elements, and/or components, but do not preclude the presence or addition of one or more other features, integers, s, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure."

A delayed fluorescence material in accordance with the present disclosure may comprise a compound having a molecular structure including an electron donor unit and an electron acceptor unit coupled to the electron donor unit. The compound having the molecular structure including the electron donor unit and the electron acceptor unit coupled to the electron donor unit may have a small difference between the singlet excited energy and triplet excited energy, such that excitons at the triplet excited energy may intersystem-cross to the singlet excited energy using a little thermal energy, thereby to lead to the delayed fluorescence.

In one embodiment, the delayed fluorescence material may include a compound having a molecular structure expressed as a following chemical formula 1, wherein, in the chemical formula 1, 'A' refers to the electron acceptor unit:

[chemical formula 1]

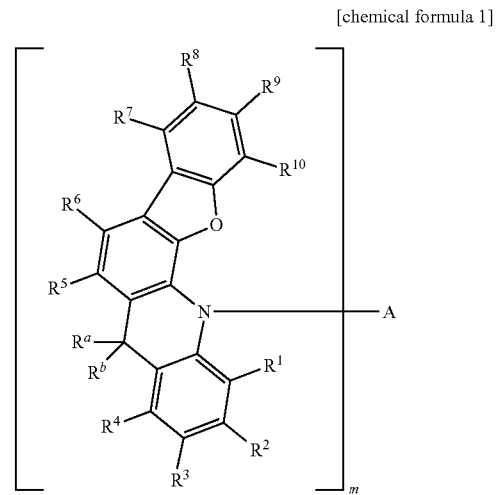

where each of $R^1$ to $R^{10}$ and $R^a$ and $R^b$ individually indicates one selected from a group consisting of hydrogen, deuterium, an alkyl group with 1 to 60 carbon atoms, an alkenyl group with 2 to 60 carbon atoms, an alkynyl group with 2 to 60 carbon atoms, an aryl group with 6 to 60 carbon atoms, a heteroaryl group with 3 to 60 carbon atoms, an alkoxy group with 1 to 60 carbon atoms, an aryloxy group with 6 to 60 carbon atoms, an arylalkyl group with 7 to 60 carbon atoms, a heteroarylalkyl group with 3 to 60 carbon atoms, a cycloalkyl group with 3 to 60 carbon atoms, a heterocycloalkyl group with 1 to 60 carbon atoms, an alkylsilyl group with 3 to 60 carbon atoms, an arylsilyl group with 3 to 60 carbon atoms, and a heteroarylsilyl group with 1 to 60 carbon atoms; and m indicates 1 or 2.

In one embodiment, all of $R^1$ to $R^{10}$ may indicate hydrogen or deuterium, and both of $R^a$ and $R^b$ may indicate methyl groups respectively.

The electron acceptor unit may act to accept the electron donated from the electron donor unit. The electron acceptor unit may be not limited specifically in terms of a material and a structure as long as it can induce a charge movement in the molecular structure of the chemical formula 1. For example, the electron acceptor unit may have, by way of example, a functional group selected from a group of functional groups expressed in a following table 1:

TABLE 1

| Acceptor | Chemical structures | HOMO [eV] | LUMO [eV] | $E_S/E_T$ [eV] |
|---|---|---|---|---|
| sulfonyldibenzene | 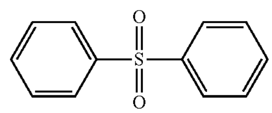 [SMILES: O=S(=O)(c1ccccc1)c1ccccc1] | −7.11 | −1.37 | 4.47/3.61 |
| benzophenone | 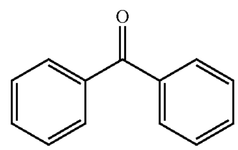 [SMILES: O=C(c1ccccc1)c1ccccc1] | −6.61 | −1.70 | 3.57/2.94 |
| 1,4-phenylenebis(phenylmethanone) | 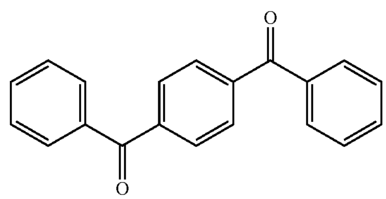 [SMILES: O=C(c1ccccc1)c1ccc(C(=O)c2ccccc2)cc1] | −6.34 | −2.23 | 3.41/2.77 |
| 1,3-phenylenebis(phenylmethanone) | 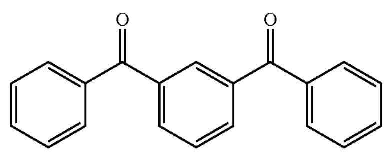 [SMILES: O=C(c1ccccc1)c1cccc(C(=O)c2ccccc2)c1] | −6.69 | −1.94 | 3.41/2.90 |
| 2,4,6-triphenyl-1,3,5-triazine | 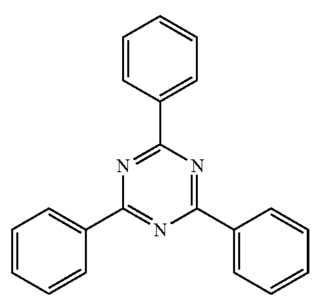 [SMILES: c1ccc(-c2nc(-c3ccccc3)nc(-c3ccccc3)n2)cc1] | −6.65 | −1.80 | 3.96/3.02 |
| benzonitrile | 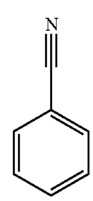 | −7.26 | −1.41 | 5.05/3.44 |
| isonicotinontrile | 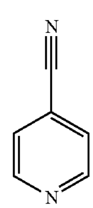 | −7.61 | −2.07 | 4.33/3.56 |

TABLE 1-continued

| Acceptor | Chemical structures | HOMO [eV] | LUMO [eV] | $E_S/E_T$ [eV] |
| --- | --- | --- | --- | --- |
| phthalonitrile | 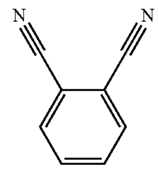 | −7.77 | −2.36 | 4.71/3.17 |
| isophthalonitrile | 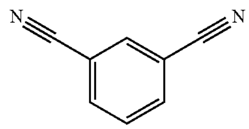 | −7.83 | −2.23 | 4.63/3.24 |
| terephthalonitrile | 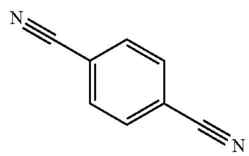 | −7.73 | −2.54 | 4.89/3.08 |
| benzene-1,3,5-tricarbonitrile | 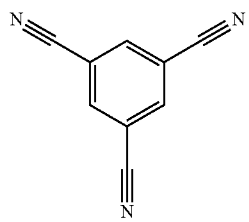 [SMILES: N#Cc1cc(C#N)cc(C#N)c1] | −8.43 | −2.83 | 4.39/3.09 |
| 4H-1,2,4-triazole | 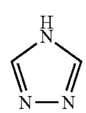 | −6.96 | 0.43 | 5.71/4.85 |
| 1,3,4-oxadiazole | 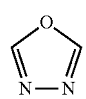 | −7.91 | −0.55 | 5.79/4.61 |
| 1,3,4-thiadiazole | 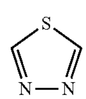 | −7.48 | −1.27 | 4.86/4.03 |
| benzo[d]thiazole | 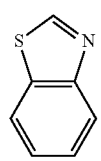 | −6.46 | −1.00 | 4.75/3.35 |
| benzo[1,2-d:4,5-d']bis(thiazole) | 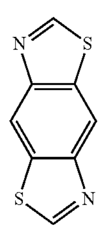 [SMILES: c1nc2cc3scnc3cc2s1] | −6.26 | −1.56 | 4.17/2.94 |
| benzo[d]oxazole | 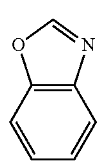 | −6.57 | −0.77 | 5.10/3.53 |

TABLE 1-continued
| Acceptor | Chemical structures | HOMO [eV] | LUMO [eV] | $E_S/E_T$ [eV] |
|---|---|---|---|---|
| benzo[1,2-d:4,5-d']bis(oxazole) | 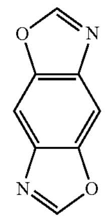 [SMILES: c1nc2cc3ocnc3cc2o1] | −6.46 | −1.32 | 4.81/3.17 |
| benzo[1,2-d:4-d']bis(oxazole) | 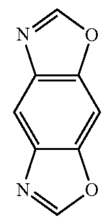 [SMILES: c1nc2cc3ncoc3cc2o1] | −6.60 | −1.20 | 4.79/3.31 |
| dibenzo[f,h]quinoxaline | 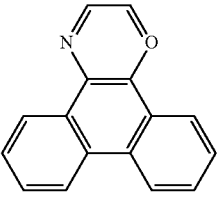 | −6.14 | −1.73 | 3.51/2.88 |
| quinoxaline | 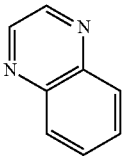 | −6.70 | −1.93 | 3.56/2.80 |
| 1H-benzo[d]imidazole | 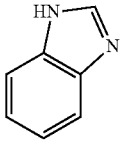 | −6.07 | −0.34 | 5.10/3.50 |
| 1,3,3a',4,6,7,9-heptaphenalene | 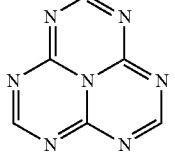 | −7.07 | −3.16 | 2.85/2.64 |
| 9H-thioxanthen-9-one 10,10-dioxide | 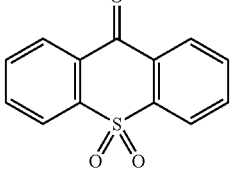 | −7.45 | −2.69 | 3.40/2.90 |
| 10,10-dimethylanthracen-9(10H)-one | 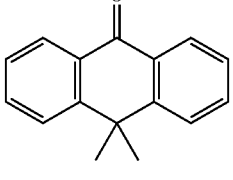 | −6.62 | −1.75 | 3.46/3.00 |

TABLE 1-continued

| Acceptor | Chemical structures | HOMO [eV] | LUMO [eV] | $E_S/E_T$ [eV] |
|---|---|---|---|---|
| anthracene-9,10-dione | 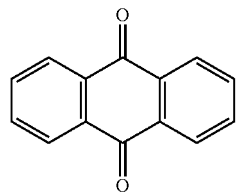 [SMILES: O=C1c2ccccc2C(=O)c2ccccc21] | −7.00 | −2.79 | 2.95/2.51 |
| 5H-cyclopenta[1,2-b:5,4-b']dipyridine | 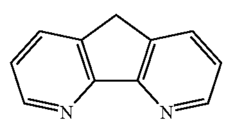 [SMILES: c1cnc2c(c1)Cc1cccnc1-2] | −6.29 | −1.33 | 3.99/3.18 |
| 9H-fluorene-2,7-dicarbonitrile | 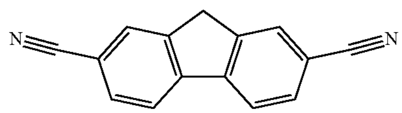 [SMILES: N#Cc1ccc2c(c1)Cc1cc(C#N)ccc1-2] | −6.72 | −2.35 | 4.03/2.70 |

In one embodiment, the electron acceptor unit may include one functional group selected from a group consisting of functional groups expressed as following chemical formulas 2 to 6 respectively:

[chemical formula 2]

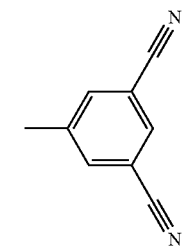

[chemical formula 3]

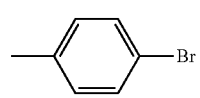

[chemical formula 4]

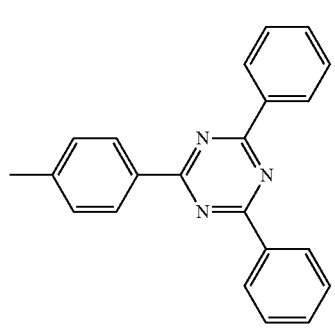

[chemical formula 5]

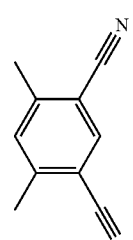

[chemical formula 6]

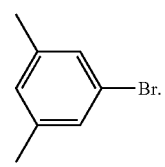

In one embodiment, the first compound has one molecular structure selected from a group of consisting of molecular structures expressed as following chemical formulas 7 to 10 respectively:

[chemical formula 7]

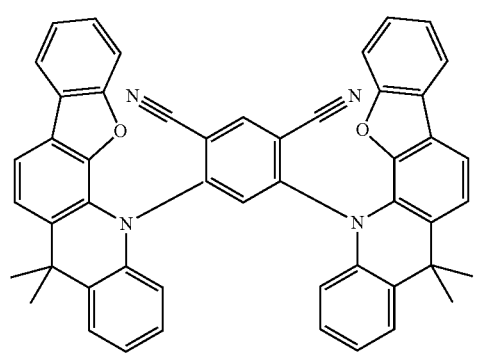

-continued

[chemical formula 8]

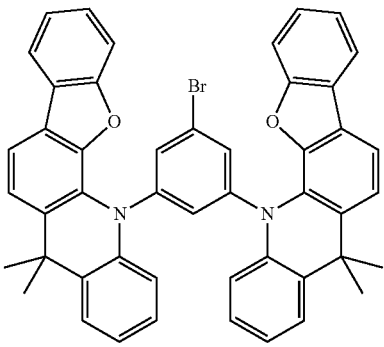

[chemical formula 9]

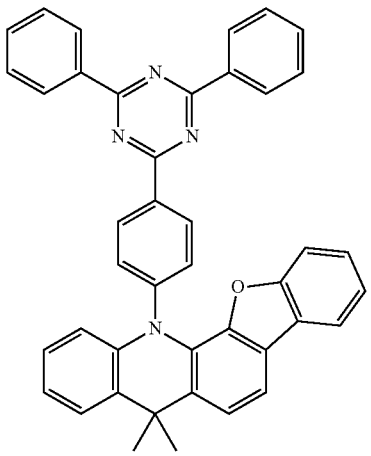

[chemical formula 10]

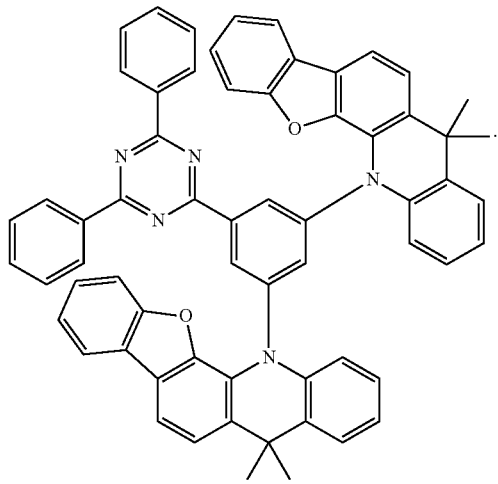

In accordance with the present disclosure, the delayed fluorescence material includes, as the electron donor unit, the acridine furan derivative formed by the acridine being bonded to a meta location of the dibenzofuran. Thus, the acridine furan derivative as the electron donor unit may have not a planar or two-dimensional structure but a three-dimensional structure, to achieve higher structural and thermal stabilities and higher triplet excited energy thereof.

Hereinafter, example embodiments will be described in more detail. The present disclosure, however, may be embodied in various different forms, and should not be construed as being limited to only the illustrated embodiments herein. Rather, these embodiments are provided as examples so that this disclosure will be thorough and complete, and will fully convey the aspects and features of the present disclosure to those skilled in the art.

Embodiment 1

[Reaction expression 1]

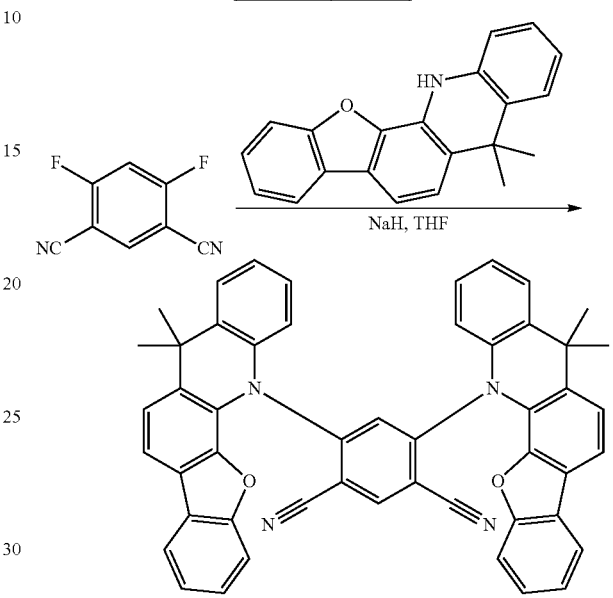

Based on the reaction expression 1, a first compound is synthesized which has a molecular structure expressed as a chemical formula of a product in the reaction expression 1 (corresponding to the above chemical formula 7).

Specifically, a sodium hydride (60% in paraffin, 0.24 g, 9.70 mmol) is washed using a nucleic acid to remove a paraffin oil. Under a nitrogen gas stream, a furan derivative acridine (1.56 g, 5.24 mmol) dissolved in tetrahydrofuran is slowly added dropwise to the purified sodium hydride. Then, the mixture has been stirred for about 30 minutes at a room temperature to acquire a first product.

Then, 4,6-difluoroisophthalonitrile (0.4 g, 2.43 mmol) is dissolved in tetrahydrofuran to acquire a second mixture which in turn is added slowly to the first product, and is agitated for about 5 hours at a room temperature, to acquire a second product.

Subsequently, water and alcohol are added to the second product to terminate the reaction. A target product is extracted using distilled water and methylene chloride. The moisture remaining in the target product is removed using magnesium sulfate. Then, the target product is subjected to the polar column chromatography using a mixture solvent of acetone and n-nucleic acid, to acquire the first compound 1.1 g. Finally, a pure yellow powder of the first compound is obtained through a final purification by sublimation by about 0.9 g (62% yield).

The final product has a following mass analysis (LC-Mass) m/z 722.85 [(M)+]. 1H NMR (400 MHZ, DMSO): δ 9.15 (s, 1H), 8.52 (s, 1H), 8.10-8.08 (d, 2H, J=4.00 Hz), 7.77-7.75 (d, 2H, J=2.00 Hz), 7.64-7.62 (m, 2H), 7.57-7.51 (m, 4H), 7.42-7.37 (m, 4H), 6.93-6.89 (t, 2H, J=5.33 Hz), 6.54-6.5 (t, 2H, J=5.33 Hz), 6.47-6.45 (d, 2H, J=4.00 Hz) 13C NMR (100 MHZ, CDCl3): δ 156.52, 150.37, 145.05, 137.71, 135.53, 134.87, 132.13, 124.85, 123.74, 121.80, 120.92, 118.78, 115.81, 11.52.

Embodiment 2

[Reaction expression 2]

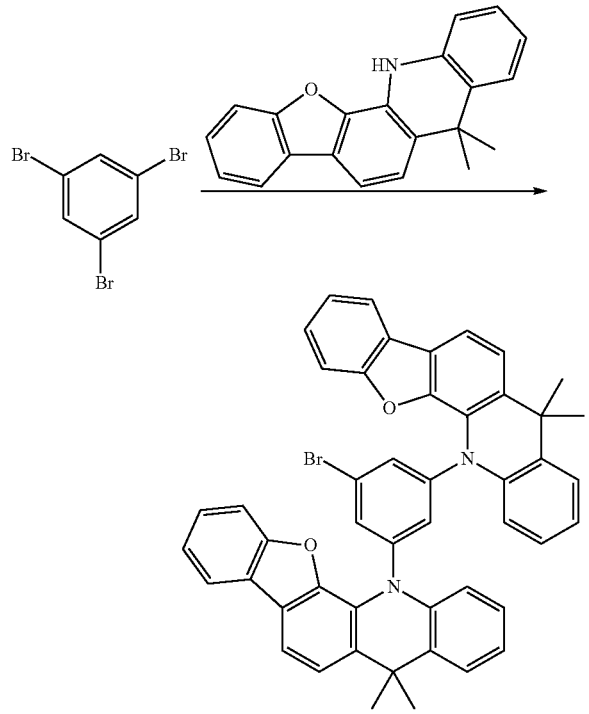

Based on the reaction expression 2, a second compound is synthesized which has a molecular structure expressed as a chemical formula of a product in the reaction expression 2 (corresponding to the above chemical formula 8).

Specifically, 1,3,5-tribromobenzene (0.60 g, 2.00 mmol) and acridine furan derivative (1.20 g, 2.00 mmol) are dried under a vacuum, and are dissolved in toluene (60.00 ml) under a stream of nitrogen in toluene to form a first solution which, in turn, receives dropwise potassium tert-butoxide (0.42 g, 4.00 mmol) dissolved in toluene to acquire a second solution. Immediately after adding a base to the second solution, the second solution changes from yellow to brown. In this state, the second solution is agitated for 20 minutes at a room temperature. Then, the second solution has palladium acetate (0.08 g, 0.20 mmol) and tert-butylphosphine 1 mole solution (1.16 ml, 5.00 mmol) added thereto in this order, to form a third solution, which, in turn, is refluxed using a heat.

Subsequently, water is added to the refluxed third solution to terminate the reaction. A target product is extracted using distilled water and methylene chloride. Then, the target product is subjected to the polar column chromatography using a mixture solvent of ethyl acetate and n-nucleic acid at a mixing ratio 1:10, to acquire a white powder 0.8 g (yield 35%) as the second compound.

The final product has a mass analysis (LC-Mass) m/z 751.71 [(M)+]. 1H NMR (400 MHZ, DMSO): δ: 7.89 (d, 2H, J=2.00 Hz), 7.66-7.64 (d, 2H, J=4.00 HZ), 7.38-7.36 (d, 2H, J=2.00 Hz), 7.32-7.31 (m, 2H), 7.17-7.14 (d, 2H, J=6.00 Hz), 7.05-7.04 (d, 2H, J=2.00 Hz), 7.02-6.98 (m, 2H), 6.75-6.74 (d, 2H, J=2.00 Hz), 6.73-6.70 (m, 2H), 6.05 (s, 2H), 5.71 (s, 1H), 6.55-6.53 (d, 2H, J=4.00 HZ)

Embodiment 3

[Reaction expression 3]

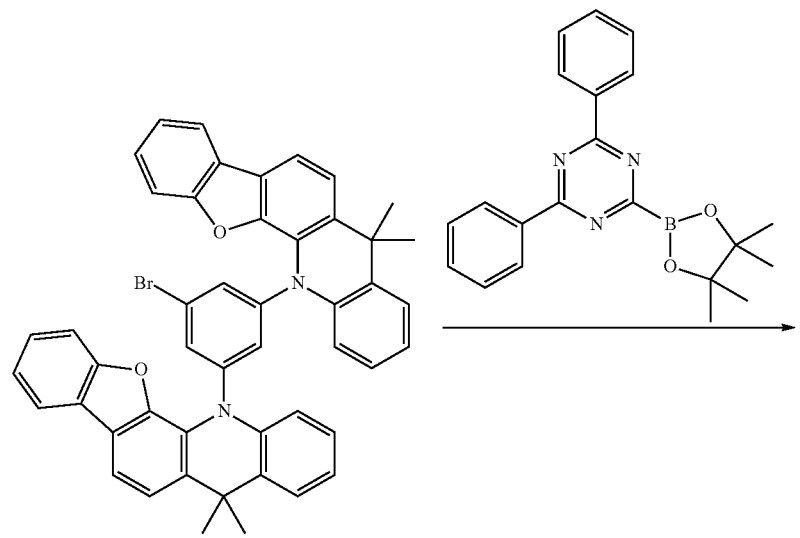

-continued

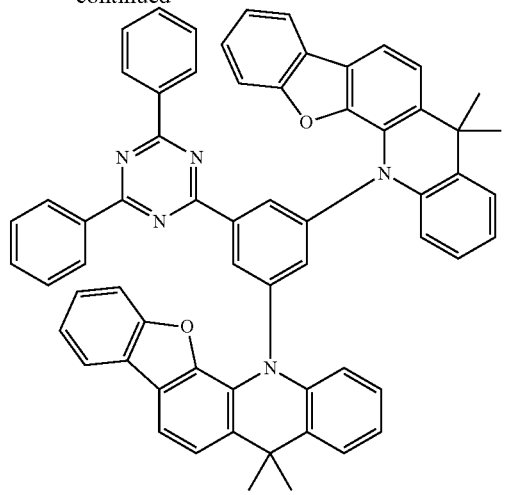

Based on the reaction expression 3, a third compound is synthesized which has a molecular structure expressed as a chemical formula of a product in the reaction expression 3 (corresponding to the above chemical formula 10).

Specifically, a mixture between 5-bromo-1,3-acridine furan derivative (0.60 g, 0.79 mmol) and 2,4-diphenyl-6-boronic ester-1,3,5-triazine (0.31 g, 0.87 mmol) is dissolved in tetrahydrofuran under a stream of nitrogen to form a first solution. The first solution is agitated for 30 minutes at a room temperature, which, in turn, has tetrakis(triphenylphosphine) palladium (0.01 g, 0.05 mmol) and potassium carbonate 2 moles aqueous solution (5.53 g) added thereto, to form a second solution, which, in turn, is refluxed using a heat.

Subsequently, water is added to the refluxed solution to terminate the reaction. A target product is extracted using distilled water and methylene chloride. Then, the target product is subjected to the polar column chromatography using a mixture solvent of ethyl acetate and n-nucleic acid, to acquire a white powder 0.4 g. Then, the white powder is subjected to purification by sublimation to acquire the third compound 0.30 g (yield 55%).

The final product has a mass analysis (LC-Mass) m/z 904.06 [(M)+]. 1H NMR (400 MHZ, DMSO): δ: 8.28-8.25 (d, 2H, J=6.00 Hz), 7.89 (d, 2H, J=2.00 Hz), 7.69-7.67 (d, 2H, J=4.00 HZ), 7.51-7.47 (m, 4H), 7.41-7.39 (m, 4H), 7.36-7.35 (d, 2H, J=2.00 Hz), 7.32-7.29 (m, 2H), 7.17-7.14 (d, 2H, J=6.00 Hz), 7.05-7.04 (d, 2H, J=2.00 Hz), 7.00-6.95 (m, 2H), 6.75-6.74 (d, 2H, J=2.00 Hz), 6.05 (s, 2H), 5.71 (s, 1H), 6.55-6.54 (d, 2H, J=4.00 HZ). 13C NMR (100 MHZ, CDCl3): δ 172.25, 170.21, 156.56, 145.03, 142.37, 135.51, 134.71, 132.10, 131.19, 130.52, 129.22, 127.56, 125.43, 124.85, 120.92, 111.50, 106.42.

Embodiment 4

[Reaction expression 4]

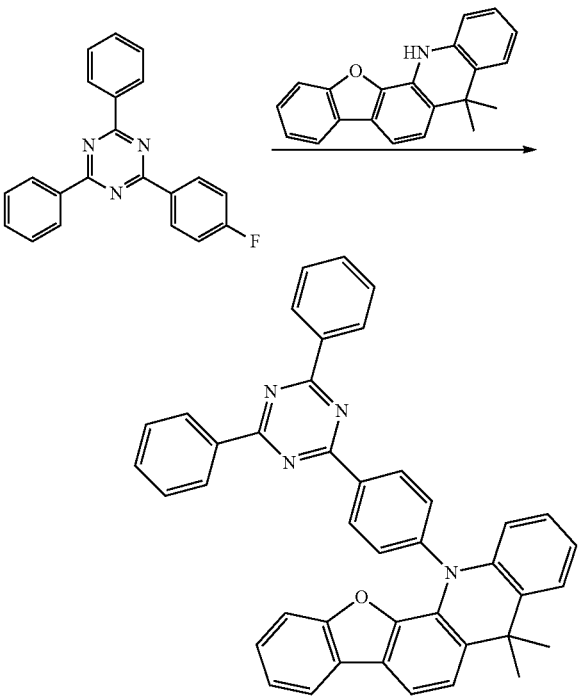

Based on the reaction expression 4, a fourth compound is synthesized which has a molecular structure expressed as a chemical formula of a product in the reaction expression 4 (corresponding to the above chemical formula 9).

Specifically, sodium hydride (0.30 g, 12.21 mmol) is washed using hexane and then is vacuum-dried. A small amount of dimethylformamide is added to the dried sodium hydride to form a first mixture. Acridine furan derivative solution (1.00 g, 136 mmol) dissolved in 20 ml dimethylformamide is added dropwise slowly to the first mixture, to form a second mixture which, in turn, is kept for 30 minutes at a room temperature. Then, 2-(4-fluorophenyl)4,6-diphenyl-1,3,5-triazine solution (1.00 g, 3.05 mmol) is added dropwise slowly to the second mixture to form a third mixture. In this connection, when 2-(4-fluorophenyl)4,6-diphenyl-1,3,5-triazine is not completely dissolved in dimethylformamide, the third mixture is refluxed using a heat applied thereto.

After 5 hours, water is added to the refluxed solution to terminate the reaction. A target product is extracted using distilled water and methylene chloride. Then, the target product is subjected to the polar column chromatography using a mixture solvent of methylene chloride and n-nucleic acid, to acquire a yellow powder 0.4 g. Then, the yellow powder is subjected to purification by sublimation as a dry purification to acquire the fourth compound 0.2 g.

The final product has a mass analysis (ASAP) m/z 606.71 [(M)+] 1H NMR (400 MHZ, DMSO): δ: 8.27-8.25 (d, 2H, J=3.80 Hz), 8.11-8.10 (d, 1H, J=1.00 Hz), 7.95-7.93 (t, 1H, J=4.00 HZ), 7.78-7.76 (m, 4H), 7.66-7.59 (m, 2H), 7.54-7.50 (m, 2H), 7.41-7.35 (m, 6H), 7.32-7.23 (m, 2H), 7.18-7.14 (t, 4H, J=4.00 HZ), 6.93-6.89 (t, 3H, J=5.33 Hz), 6.47-6.45 (d, 3H, J=4.00 Hz) 13C NMR (100 MHZ, CDCl3): δ 172.21, 170.25, 156.86, 143.03, 140.27, 133.55, 134.11, 132.80, 131.14, 130.23, 128.18, 126.26, 124.73, 122.25, 120.12, 113.20, 104.72.

Example

Delayed fluorescence light emitting devices 100 are manufactured to include light emitting layers containing first and third compounds produced according to the embodiment 1 to embodiment 3 respectively. Each of the delayed fluorescence light emitting devices 100 may have a configuration as shown in FIG. 1. The delayed fluorescence light emitting devices 100 are measured in terms of a maximum quantum efficiency and light emitting color space thereof.

The delayed fluorescence light emitting device 100 may include, on a substrate 110, a positive electrode 120, a hole injection layer 130, a hole transport layer 140, a light emitting layer 150, an electron transport layer 160, an electron injection layer 170 and a negative electrode 180, which may be sacked in this order using a vacuum deposition. In this connection, the positive electrode 120, hole injection layer 130, hole transport layer 140, electron injection layer 170 and negative electrode 180 may be made of ITO, PEDOT: PSS (poly(3,4-ethylenedioxythiophene); poly(styrenesulfonate)), TAPC (4,4'-cyclohexylidenebis[N,N-bis(4-methylphenyl)aniline]), TPBi (1,3,5-tris(N-phenylbenzimidazole-2-yl)benzene), lithium fluoride (LiF) and aluminum (Al) respectively. The electron transport layer 160 may be formed of a stack of a first layer made of TSPO1 (diphenyl(4-(triphenylsilyl)phenyl)phosphine oxide) and a second layer made of TPBI (1,3,5-tris(N-phenylbenzimidazole-2-yl)benzene) on the light emitting layer 150.

The light emitting layer 150 including the first compound of the embodiment 1 is formed by mixing the first compound and mCP (1,3-bis(N-carbazolyl)benzene) and TPBI each other. In this connection, the first compound is doped to the mCP (1,3-bis(N-carbazolyl)benzene) and TPBI at 10% concentration.

The light emitting layer 150 including the second compound of the embodiment 2 is formed by mixing the second compound and mCP (1,3-bis(N-carbazolyl)benzene) and TPBI each other. In this connection, the second compound is doped to the mCP (1,3-bis(N-carbazolyl)benzene) and TPBI at 10% concentration.

The light emitting layer 150 including the third compound of the embodiment 2 is formed by mixing the third compound and mCP (1,3-bis(N-carbazolyl)benzene) and TPBI each other. In this connection, the third compound is doped to the mCP (1,3-bis(N-carbazolyl)benzene) and TPBI at 10% concentration.

A following table 2 shows maximum quantum efficiency and light emitting color space measurements of the light emitting device (hereinafter, a light emitting device 1) including the light emitting layer containing the first compound, the light emitting device (hereinafter, a light emitting device 2) including the light emitting layer containing the second compound, and the light emitting device (hereinafter, a light emitting device 3) including the light emitting layer containing the third compound.

TABLE 2

|  | Color space (x, y) | Maximum quantum efficiency (%) |
| --- | --- | --- |
| Light emitting device 1 | 0.28, 0.57 | 17.0 |
| Light emitting device 2 | 0.37, 0.50 | 15.9 |
| Light emitting device 3 | 0.18, 0.35 | 15.1 |

Referring to the table 2, the light emitting device 1 emits a green light beam at a color space (0.28, 0.57), and has a maximum quantum efficiency 17.0%; the light emitting device 2 emits a green light beam at a color space (0.37, 0.50) and has a maximum quantum efficiency 15.9%; and the light emitting device 3 emits a green light beam at a color space (0.18, 0.35) and has a maximum quantum efficiency 15.1%.

Thus, the use of the delayed fluorescence materials of all of the embodiments of the present disclosure as the light emitting material may achieve the notably improved maximum quantum efficiency.

The above description is not to be taken in a limiting sense, but is made merely for the purpose of describing the general principles of exemplary embodiments, and many additional embodiments of this disclosure are possible. It is understood that no limitation of the scope of the disclosure is thereby intended. The scope of the disclosure should be determined with reference to the Claims. Reference throughout this specification to "one embodiment," "an embodiment," or similar language means that a particular feature, structure, or characteristic that is described in connection with the embodiment is included in at least one embodiment of the present disclosure. Thus, appearances of the phrases "in one embodiment," "in an embodiment," and similar language throughout this specification may, but do not necessarily, all refer to the same embodiment.

What is claimed is:
1. A delayed fluorescence material comprising
   a first compound having a molecular structure including an electron donor unit and an electron acceptor unit, comprising one or more of a nitrile, bromobenzene, azole, or polycyclic group, coupled to the electron donor unit,
   wherein the electron donor unit includes an acridine furan derivative having dibenzofuran and acridine bonded to the dibenzofuran.
2. The delayed fluorescence material of claim 1, wherein the first compound has a molecular structure expressed as a following chemical formula 1:

[chemical formula 1]

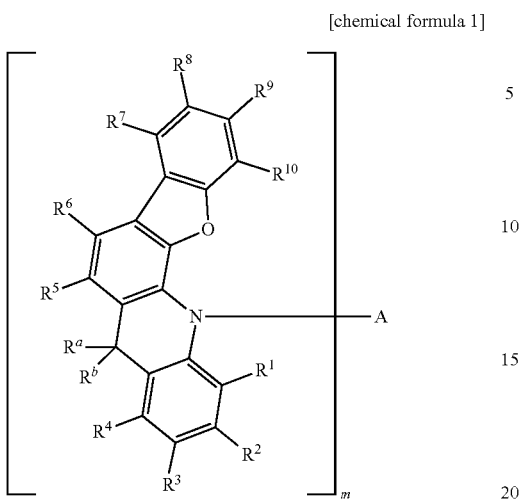

where, A indicates the electron acceptor unit; each of $R^1$ to $R^{10}$ and $R^a$ and $R^b$ individually indicates one selected from a group consisting of hydrogen, deuterium, an alkyl group with 1 to 60 carbon atoms, an alkenyl group with 2 to 60 carbon atoms, an alkynyl group with 2 to 60 carbon atoms, an aryl group with 6 to 60 carbon atoms, a heteroaryl group with 3 to 60 carbon atoms, an alkoxy group with 1 to 60 carbon atoms, an aryloxy group with 6 to 60 carbon atoms, an arylalkyl group with 7 to 60 carbon atoms, a heteroarylalkyl group with 3 to 60 carbon atoms, a cycloalkyl group with 3 to 60 carbon atoms, a heterocycloalkyl group with 1 to 60 carbon atoms, an alkylsilyl group with 3 to 60 carbon atoms, an arylsilyl group with 3 to 60 carbon atoms, and a heteroarylsilyl group with 1 to 60 carbon atoms; and m indicates 1 or 2.

3. The delayed fluorescence material of claim 2, wherein each of $R^1$ to $R^{10}$ indicates hydrogen or deuterium and both of $R^a$ and $R^b$ indicate methyl groups respectively.

4. The delayed fluorescence material of claim 2, wherein the electron acceptor unit comprises one functional group selected from a group consisting of functional groups expressed as following chemical formulas 2 to 6:

[chemical formula 2]

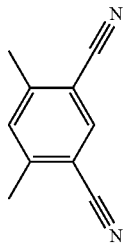

[chemical formula 3]

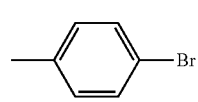

[chemical formula 4]

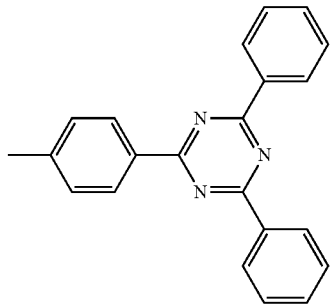

[chemical formula 5]

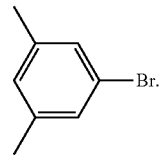

[chemical formula 6]

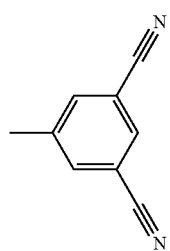

5. The delayed fluorescence material of claim 1, wherein the first compound has one molecular structure selected from a group of consisting of molecular structures expressed as following chemical formulas 7 to 10 respectively:

[chemical formula 7]

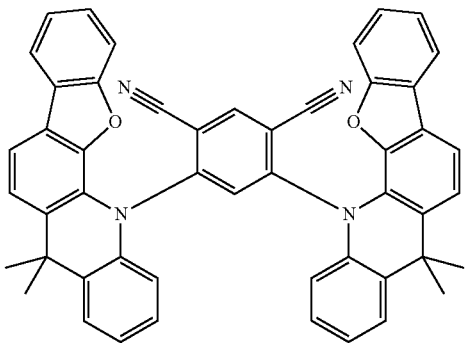

[chemical formula 8]

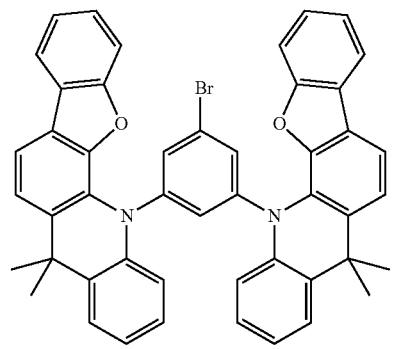

[chemical formula 9]

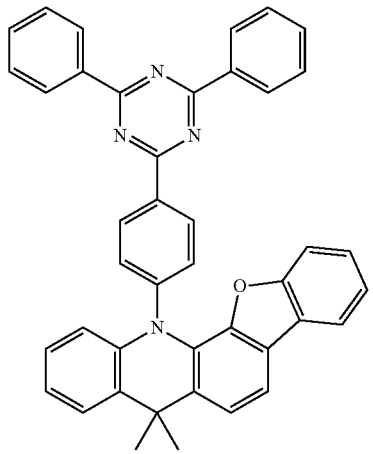

[chemical formula 10]

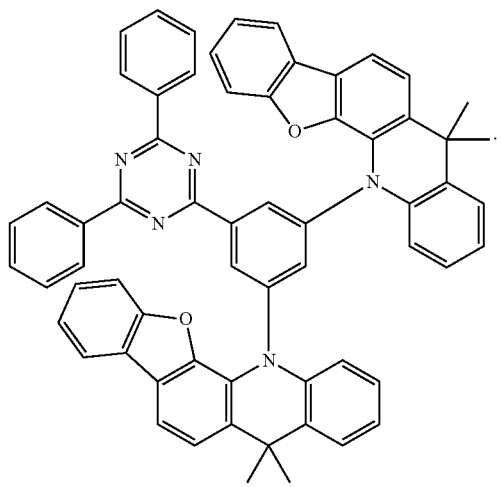

6. An organic light emitting device comprising a light emitting layer containing the delayed fluorescence material of claim 1.

7. An organic light emitting device comprising a light emitting layer containing the delayed fluorescence material of claim 2.

8. An organic light emitting device comprising a light emitting layer containing the delayed fluorescence material of claim 3.

9. An organic light emitting device comprising a light emitting layer containing the delayed fluorescence material of claim 4.

10. An organic light emitting device comprising a light emitting layer containing the delayed fluorescence material of claim 5.

11. A delayed fluorescence material comprising
a first compound having a molecular structure including an electron donor unit and an electron acceptor unit coupled to the electron donor unit,
wherein the electron donor unit includes an acridine furan derivative having dibenzofuran and acridine bonded to the dibenzofuran;
wherein the first compound has a molecular structure expressed as a following chemical formula 1:

[chemical formula 1]

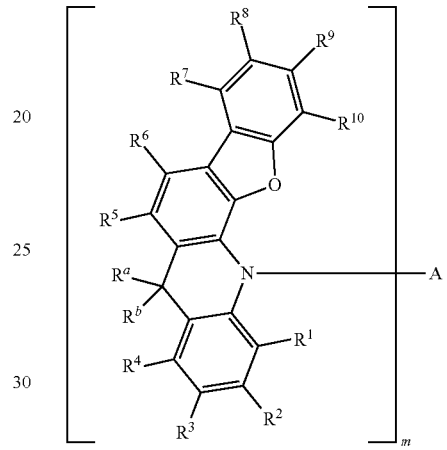

where, A indicates the electron acceptor unit; each of $R^1$ to $R^{10}$ and $R^a$ and $R^b$ individually indicates one selected from a group consisting of hydrogen, deuterium, an alkyl group with 1 to 60 carbon atoms, an alkenyl group with 2 to 60 carbon atoms, an alkynyl group with 2 to 60 carbon atoms, an aryl group with 6 to 60 carbon atoms, a heteroaryl group with 3 to 60 carbon atoms, an alkoxy group with 1 to 60 carbon atoms, an aryloxy group with 6 to 60 carbon atoms, an arylalkyl group with 7 to 60 carbon atoms, a heteroarylalkyl group with 3 to 60 carbon atoms, a cycloalkyl group with 3 to 60 carbon atoms, a heterocycloalkyl group with 1 to 60 carbon atoms, an alkylsilyl group with 3 to 60 carbon atoms, an arylsilyl group with 3 to 60 carbon atoms, and a heteroarylsilyl group with 1 to 60 carbon atoms; and m indicates 1 or 2; and wherein the electron acceptor unit comprises one functional group selected from a group consisting of functional groups expressed as following chemical formulas 2 to 6:

[chemical formula 2]

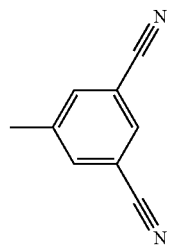

-continued

[chemical formula 3]

[chemical formula 4]

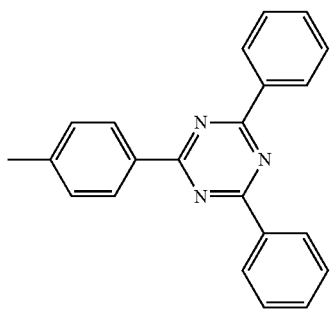

[chemical formula 5]

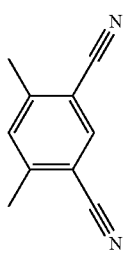

[chemical formula 6]

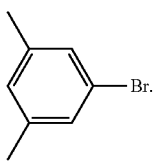

12. An organic light emitting device comprising a light emitting layer containing the delayed fluorescence material of claim 11.

13. A delayed fluorescence material comprising
a first compound having a molecular structure including an electron donor unit and an electron acceptor unit coupled to the electron donor unit,
wherein the electron donor unit includes an acridine furan derivative having dibenzofuran and acridine bonded to the dibenzofuran;
wherein the first compound has a molecular structure expressed as a following chemical formula 1:

[chemical formula 1]

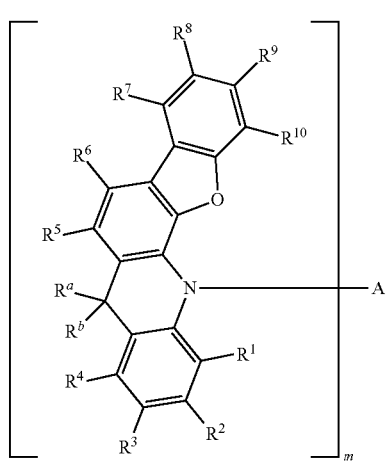

where, A indicates the electron acceptor unit; each of $R^1$ to $R^{10}$ and $R^a$ and $R^b$ individually indicates one selected from a group consisting of hydrogen, deuterium, an alkyl group with 1 to 60 carbon atoms, an alkenyl group with 2 to 60 carbon atoms, an alkynyl group with 2 to 60 carbon atoms, an aryl group with 6 to 60 carbon atoms, a heteroaryl group with 3 to 60 carbon atoms, an alkoxy group with 1 to 60 carbon atoms, an aryloxy group with 6 to 60 carbon atoms, an arylalkyl group with 7 to 60 carbon atoms, a heteroarylalkyl group with 3 to 60 carbon atoms, a cycloalkyl group with 3 to 60 carbon atoms, a heterocycloalkyl group with 1 to 60 carbon atoms, an alkylsilyl group with 3 to 60 carbon atoms, an arylsilyl group with 3 to 60 carbon atoms, and a heteroarylsilyl group with 1 to 60 carbon atoms; and m indicates 1 or 2; and wherein the first compound has one molecular structure selected from a group of consisting of molecular structures expressed as following chemical formulas 7 to 10 respectively:

[chemical formula 7]

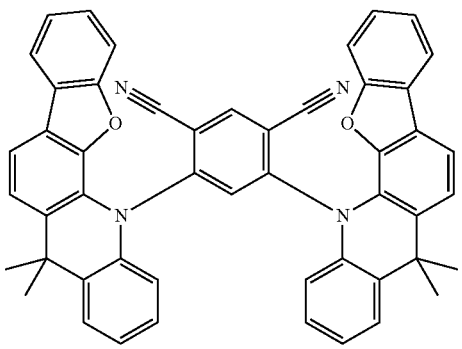

[chemical formula 8]

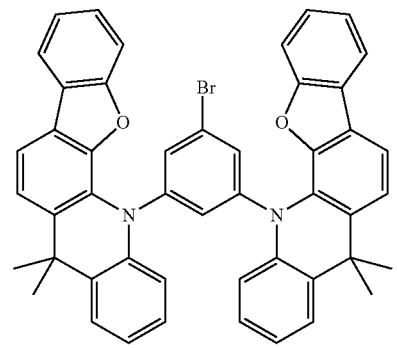

[chemical formula 9]

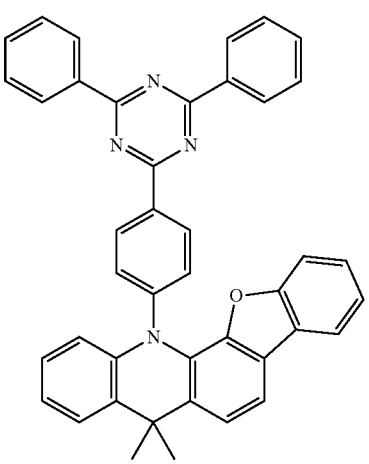

-continued
[chemical formula 10]
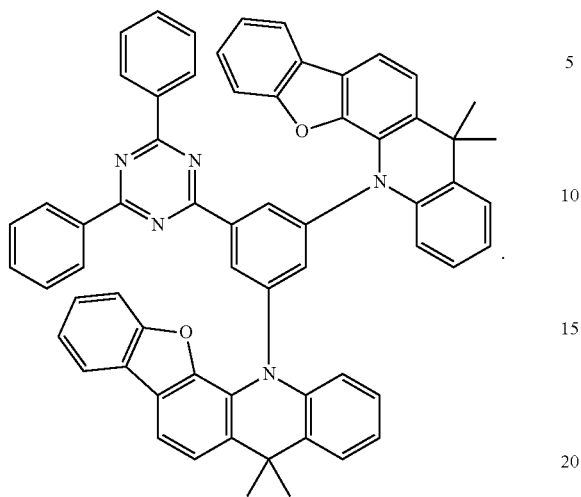
14. An organic light emitting device comprising a light emitting layer containing the delayed fluorescence material of claim 13.
* * * * *